United States Patent [19]

Chao et al.

[11] Patent Number: 4,996,007

[45] Date of Patent: Feb. 26, 1991

[54] PROCESS FOR THE OXIDATION OF ALCOHOLS TO ALDEHYDES/ACIDS/ESTERS

[75] Inventors: Kuo-Hua Chao; Tamal K. Dutta, both of Houston; Lynn H. Slaugh, Cypress, all of Tex.

[73] Assignee: Shell Oil Company, Houston, Tex.

[21] Appl. No.: 467,118

[22] Filed: Jan. 19, 1990

[51] Int. Cl.$^5$ .......................... C11C 3/02; C11C 1/00; C07C 69/02; C07C 69/66
[52] U.S. Cl. .......................... 260/410.9 R; 260/413 J; 560/231; 560/187; 562/538; 568/471
[58] Field of Search .......................... 260/410.9, 413 J; 560/231, 187; 562/538; 568/471

[56] References Cited

U.S. PATENT DOCUMENTS

| | | | |
|---|---|---|---|
| 3,346,626 | 3/1966 | Schaeffer et al. | 560/243 |
| 4,052,424 | 10/1977 | Vanderspurt | 260/410.9 R |
| 4,126,748 | 11/1978 | Scholz et al. | 562/538 |

OTHER PUBLICATIONS

Yokota et al., Japan Kokai 62,212,350, Sep. 18, 1987, Chemical Abstracts, vol. 109, 1988 Abstract 210517u.

*Primary Examiner*—Mukund J. Shah
*Assistant Examiner*—E. C. Ward

[57] ABSTRACT

The instant invention relates to a process for the oxidation of primary alcohols to aldehydes, acids and esters, particularly to aldehydes. In this process and alcohol and oxygen are contacted and reacted with a dihydrodihydroxynaphthalene or a dihydrodihydroxyanthracene in the presence of a Group VIII metal oxidation catalyst and optionally in the presence of a quaternary ammonium halide cocatalyst, and subsequently product aldehyde/acid/ester and the corresponding napthoquinone or anthraquinone are separated from the reaction mixture. The by-product naphthoquinone or anthraquinone is suitably recycled to the alcohol oxidation step by hydrogenating the naphthoquinone or anthraquinone to the corresponding dihydrodihydroxynaphthalene or dihydrodihydroxyanthracene by contacting it with hydrogen in the presence of a hydrogenation catalyst.

7 Claims, No Drawings

PROCESS FOR THE OXIDATION OF ALCOHOLS TO ALDEHYDES/ACIDS/ESTERS

FIELD OF THE INVENTION

This invention relates to a process for the oxidation of alcohols to aldehydes/acids/esters using molecular oxygen.

BACKGROUND OF THE INVENTION

Alcohols, particularly primary alcohols, are readily available in large commercial quantities. Processes to convert primary alcohols to aldehydes, acids and esters fill a useful need in the industrial world. Processes such as direct oxidation with air or with nitric acid are available to convert alcohols to aldehydes and acids. These processes require extreme control in order to prevent over-oxidation. There is a need for a process that will operate at low temperatures to prevent the formation of degradation products and can be easily controlled. Processes that produce high yields of aldehydes are particularly desired.

SUMMARY OF THE INVENTION

The instant invention relates to a process for the oxidation of primary alcohols to aldehydes, acids and esters, particularly to aldehydes, which comprises contacting and thereby reacting an alcohol and oxygen with a dihydrodihydroxynaphthalene or a dihydrodihydroxyanthracene in the presence of an oxidation catalyst comprising a Group VIII metal and optionally in the presence of a cocatalyst comprising a quaternary ammonium halide, and subsequently separating from the reaction mixture product aldehyde/acid/ester and the corresponding napthoquinone or anthraquinone. The by-product naphthoquinone or anthraquinone is suitably recycled to the alcohol oxidation step by hYdrogenating the naphthoquinone or anthraquinone to the corresponding dihydrodihydroxynaphthalene or dihydrodihydroxyanthracene by contacting it with hydrogen in the presence of a hydrogenation catalyst.

DETAILED DESCRIPTION OF THE INVENTION

The instant process comprises reacting a primary alcohol with molecular oxygen to produce aldehydes, acids and esters in the presence of an oxygen activator which promotes the reaction, an oxidation catalyst comprising a Group VIII metal and, optionally, a cocatalyst comprising a quaternary ammonium halide.

The process makes use of a recyclable oxygen activator. This activator activates oxygen thereby causing it to react with a primary alcohol at relatively mild conditions and thus converting it to aldehydes/acids/esters while at the same time the activator is concomitantly oxidized. The oxidized activator ("activator-precursor") is then reduced with hydrogen back to its original state and recycled back to the alcohol oxidation step.

The oxygen activator-precursor utilized herein is naphthoquinone, and/or anthraquinone. As used herein the naphthoquinones and anthraquinones and the corresponding reduced hydroxy compounds are meant to include substituted as well as unsubstituted compounds, that is, substituted with substituents in addition to the required keto, hydro and hydroxy substituents. Non-limiting examples of such substituents include lower alkyl, such as methyl and ethyl, halo, nitro, sulfonate, etc. Preferred substituents are those having electron withdrawing capacity. Electron-withdrawing substituent groups are well known to those skilled in the chemical arts and include by way of non-limiting examples $-N(CH_3)_3^{30}$, $-NO_2$, $-CN$, $-SO_3H$, $-SO_3^-$, $-COOH$, $-COO^-$, $-CHO$, $-X$ (halo), $-OCF_3$, etc. The particular substituent utilized should be inert under the reaction conditions and relatively small, such that it does not provide so much steric hindrance that the oxygen activation reaction step is inhibited. Suitable substituted naphthoquinones and anthraquinones can be determined by routine experimentation. The oxygen activator-precursor is usually more readily obtained or synthesized than is the oxygen activator, and typically the activator is obtained by reducing the activator-precursor with hydrogen in the presence of a reducing catalyst. In effect, the instant process utilizes an oxidation/reduction cycle to recycle an oxygen activator comprising dihydrodihydroxynaphthalene or dihydrodihydroxyanthracene from the corresponding activator-precursor comprising naphthoquinone or anthraquinone and back again.

The oxygen activator may be utilized in a one-phase hydrocarbon system or in a two-phase hydrocarbon/water system. The solubility of the activator in the aqueous phase will depend on the presence of water solubilizing substituents on the activator, such as sulfonate substituent(s), particularly the alkali metal sulfonates. The use of a two phase system can have certain processing advantages, particularly when the activator is more soluble in the aqueous phase than in the hydrocarbon phase and the alcohol and product aldehydes, acids and esters are more soluble in the hydrocarbon phase than in the aqueous phase. In the latter case the organic phase contains the unreacted alcohol and the maJor portion of the produced aldehyde/acid/ester and the aqueous phase contains the oxygen activator and activator-precursor and a residual amount of product aldehyde/acid/ester, which will allow a ready separation of product aldehyde/acid/ester and reactant alcohol from the oxygen activator/precursor. Long chain alcohols are suitably processed with this two phase system.

In addition to the use of water as a solvent as indicated above, other organic solvents can be utilized, such as alkanes, aromatics, such as benzene, toluene and xylene; alkanes, halo-substituted aromatics, amides, amines, ethers, sulfoxides, etc.. Solvents selected should not react with either the reactant alcohol or the product aldehyde/acid/ester.

Molecular oxygen is utilized to oxidize the alcohol to product aldehyde/acid/ester. While pure oxygen can be utilized, it does pose problems with flammability and more dilute concentrations of oxygen are preferably utilized. Preferably air is utilized as the source of molecular oxygen.

An oxidation catalyst is utilized in the reaction to oxidize the alcohol to aldehyde/acid/ester. The oxidation catalysts utilized in the instant process are traditional oxidation catalysts used in the art to oxidize organic compounds. Non-limiting examples of these oxidation catalysts comprise vanadium, chromium, manganese, iron, cobalt, copper, yttrium, niobium, molybdenum, ruthenium, rhodium, palladium, silver, the lanthanide series, rhenium, osmium, bismuth, thorium, uranium, tungsten, mercury, lead, titanium, thallium, etc. Preferred catalysts are selected from the group consisting of ruthenium, rhodium, platinum, palladium, rhenium and mixtures thereof. The oxidation catalyst may be homogeneous or heterogeneous. When the catalyst is homogeneous, it is preferred that a two phase system be utilized and that the catalyst be soluble in the aqueous phase in order to facilitate separation of the catalyst from the product aldehyde/acid/ester concentrated in the organic phase. Heterogeneous catalysts are preferred as they are readily separated from unreacted feed and product. Heterogeneous catalysts comprise catalytic metals on inert porous supports, such as the refractory oxide supports or carbon. Preferred supports for heterogeneous catalysts are alumina and carbon.

A cocatalyst comprising a quaternary ammonium halide is optionally utilized. Preferably the cocatalyst is quaternary alkyl ammonium halide wherein the alkyl moieties have carbon numbers ranging from 1 to about 20. Higher alkyl ammonium bromides are preferred.

The alcohol oxidation reaction may be carried out in a batch reactor or in a continuous flow reactor. For example, it may be carried out in a fixed bed reactor, the bed comprising the catalyst, wherein the alcohol and the oxygen activator is passed over the bed in the presence of an oxygen-containing gas. Alternatively, the alcohol and the oxygen activator may be trickled over a bed of inert support materials, such as alumina raschig rings or berl saddles, in the presence of an oxygen-containing gas and in the presence of a homogenous oxidation catalyst. Other continuous reactor configurations will be readily apparent to one skilled in the art.

Batch reactors, such as autoclaves, are also suitable. For example, the primary alcohol, an aqueous solution of the oxygen activator and an oxidation catalyst can be loaded into an autoclave, the autoclave sealed and charged with an oxygen-containing gas, heated to a desired reaction temperature and the reaction allowed to proceed.

Reaction pressures for the instant process are not critical and will typically range from about atmospheric to about 100 atmospheres, although higher and lower pressures can be utilized. The reaction temperature of the instant process depends, inter alia, upon the particular oxidation catalyst utilized, but will typically range from about 0° C. to about 100° C., preferably from about 25° C. to about 75° C.

For the two-phase system, after reaction there will be an hydrocarbon phase containing unreacted alcohol and the major portion of the product aldehyde/acid/ester. The hydrocarbon phase may be diluted with a inert organic solvent, such as an alkane. There will also be an aqueous phase containing the oxidized oxygen activator, a small amount of alcohol and product aldehyde/acid/alcohol and the oxidation catalyst if it is homogeneous. The hydrocarbon phase is processed, say by distillation, to recover the product aldehyde/acid/ester. The aqueous phase may also be processed to remove any residual alcohol or aldehyde/acid/ester, say by liquid-liquid extraction with an organic solvent.

For the single phase hydrocarbon system, after reaction, the hydrocarbon phase is processed by conventional techniques such as distillation, liquid-liquid extraction with water, filtration, etc., in order to separate the product aldehyde/acid/ester, the oxidized activator, unreacted alcohol and any oxidation catalyst and cocatalyst.

It is a particular advantage of the instant process that the oxidized oxygen activator can be reduced by contact with hydrogen and a hydrogenation catalyst to regenerate the oxygen activator. The regenerated oxygen activator can then be conveniently recycled to the alcohol oxidation reactor. The hydrogenation catalyst used to reduce the oxidized oxygen activator can be any of the conventional hydrogenation catalysts that are useful for hydrogenating organic compounds. Non-limiting examples of these hydrogenation catalysts comprise iron, cobalt, nickel, copper, osmium, platinum, palladium, rhodium, ruthenium, tin, iridium, etc.. The hydrogenation catalyst may be homogeneous or heterogeneous. However, a heterogeneous catalyst is preferred since it can more readily be separated from the regenerated oxygen activator prior to its recycle to the alcohol oxidation reactor. A preferred catalyst is palladium dispersed on an inert support such as carbon or alumina. Reaction pressures for the hydrogenation are not critical and will typically range from about atmospheric to about 100 atmospheres, although higher and lower pressures can be utilized. The reaction temperature will depend upon the particular hydrogenation catalyst utilized, but will typically range from about 0° C. to about 100° C., preferably from about 25° C. to about 75° C. Under certain conditions the hydrogenation catalyst can also serve as the optional oxidation catalyst.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be described by the following examples which are provided for illustrative purposes and are not to be construed as limiting the invention.

EXPERIMENTAL PROCEDURE

In a typical experiment a mini Parr autoclave (100 ml capacity), equipped with a glass liner, was charged in dry box (pre-purified nitrogen-gas purged) with 15.0 milliliters of solvent (for example, 1,2-dichloroethane); 8.0 mmols of substrate (for example, 1-dodecanol, 1.55 g); 16.0 mmols of oxygen-activator precursor (for example, 2-ethylanthraquinone, 4.0 g); 0.06 mmols of transition-metal catalyst (for example, 5% Pd/C., 0.12g)., and 2 mmols of quaternary ammonium halide (for example, didecyldimethylammonium bromide, 0.94g).

The autoclave was then sealed securely and stirred magnetically. Then nitrogen gas was flushed out by hydrogen gas (for example, 450 psi hydrogen gas pressure). The autoclave was heated to 40° C. in order to effectuate hydrogenation of the oxygen-activator precursor to the oxygen-activator. Hydrogenation was monitored by recording the drop of hydrogen gas pressure with time until there was no recordable drop in hydrogen gas pressure. The final hydrogen gas pressure was noted. About a 50 psi pressure drop at room temperature was recorded for this scale of reactants. The residual hydrogen gas was vented out, flushed three times with pre-purified nitrogen gas, and finally replaced by compressed air (for example, 600 psi).

The autoclave was then heated to 60° C. (internal temperature) and the drop of air pressure with time was recorded with time until there was no more recordable change in air pressure (usually about 18 hours). The hot autoclave was then allowed to cool down to room temperature and the final air pressure was recorded. The net air pressure drop at room temperature for this scale of reactants was about 150 psi. The residual air was then vented out. The autoclave was then opened in dry box and the reaction product mixture was filtered through a coarse glass-frit to separate the solution of the crude reaction product mixture form the suspended materials (the recovered catalyst).

The solution of the crude reaction product mixture was then analyzed by gas liquid chromatography (GLC) using a Hewlett-Packard 5890A gas chromatograph fitted with a hydrogen flame ionization detector and a data processor. The peaks of the chromatograms were identified qualitatively by comparison of their retention times with those of standards and by GC/MS technique. The quantitative estimation of the percent composition of the reaction mixture was obtained from the integration of the areas of the peaks in the chromatograms.

ILLUSTRATIVE EMBODIMENT I

Following the experimental procedure described above experiments were carried out on two different alcohol substrates: 1-dodecanol and 1-dodecanol which had been ethoxylated with one mole of ethylene oxide (on the average). The experimental conditions and the results are shown in Table 1 below. As used herein the term "Neodol" as applied to alcohols is a registered trademark of Shell Oil Company.

TABLE 1

| Oxidation of Alcohol: Nature of the Substrate | | | | | |
|---|---|---|---|---|---|
| | | Conver- | Selectivity, % | | |
| Substrate | Cocatalyst | sion, % | Aldehyde | Acid | Ester |
| 1-Dodecanol | DDAB | 74.0 | 95.0 | — | — |
| Noedol (EO)$_1$* | DDAB | 63.0 | 17.0 | 6.0 | — |

| Conditions | |
|---|---|
| Solvent | 1,2-Dichloroethane, 15 mls. |
| Cocatalyst | DDAB is Didecyldimethylammonium bromide, 0.94 g (2 mmols) |
| Catalyst | Ru(10%)/Al$_2$O$_3$, 1.19 g |
| Oxidant | Air/2-Ethyl-9,10-dihydro-9,10-dihydroxyanthracene |
| Oxidation Temp. | 70° C. |
| Air Pressure | 600–800 psi |
| Hydrogenation Temp. | 40°–60° |
| Hydrogen Press. | 450 psi |
| Oxidation Reaction Time | 18 hrs. |

*Neodol (EO)$_1$ - CH$_3$—(CH$_2$)$_{11}$—(—O—CH$_2$—CH$_2$)$_1$—OH

ILLUSTRATIVE EMBODIMENT II

Utilizing the above-described experimental procedure, different oxygen-activators were used. The experimental conditions and the results are shown in Table 2 below (autoclave experiments).

TABLE 2

| Oxidation of 1 - Dodecanol: Effect of O$_2$ - Activator | | | | |
|---|---|---|---|---|
| | Conver- | Selectivity, % | | |
| O$_2$ - Activator | sion, % | C$_{12}$-Aldehyde | C$_{12}$-Acid | C$_{24}$-Ester |
| 1 | 74.0 | 95.0 | — | — |
| 2 | 57.0 | 83.0 | 6.0 | 1.0 |
| 3 | 29.0 | 82.0 | — | 14.0 |
| 4 | 7.0 | 67.0 | — | — |

| Conditions: | |
|---|---|
| Substrate | 1-Dodecanol, 1.55 g (8 mmols) |
| Solvent | 1,2-Dichloroethane, 15 mls. |
| Cocatalyst | DDAB is Didecyl dimethylammonium bromide, 0.94 g (2 mmols) |
| Catalyst | Ru(10%)/Al$_2$O$_3$(0.10–0.20 g) |
| Oxidation Temp. | 70° C. |
| Air Pressure | 600–800 psi |
| Hydrogenation Temp. | 40°–60° |
| Hydrogen Pressure | 450 psi |
| Oxidation Reaction Time | 18 hrs. |

1: 2-Ethyl-9,10-dihydro-9,10-dihydroxyanthracene, 4.2 g (17.7 mmols)
2: 2,3-Dichloro-1,4-dihydro-1,4-dihydroxynapthalene, 3.8 g (16.9 mmols)
3: 6,7-Dichloro-1,4,9,10-tetrahydro-1,4,9,10-tetrahydroxyanthracene, 4.9 g (16.1 mmols)
4: 9,10-Dihydro-9,10-dihydroxyanthracene-2,6-disulfonic acid, disodium salt, 6.7 g (16.3 mmols)

ILLUSTRATIVE EMBODIMENT III

Utilizing the above-described experimental procedure, different oxidation catalysts were used. The experimental conditions and the results are shown in Table 3 below (autoclave experiments).

TABLE 3

| Oxidation of 1-Dodecanol: Effect of catalyst | | | | |
|---|---|---|---|---|
| | Conver- | Selectivity, % | | |
| Catalyst | sion, % | C$_{12}$-Aldehyde | C$_{12}$-Acid | C$_{24}$-Ester |
| Ru(10%)/Al$_2$O$_3$ (0.19 g) | 74.0 | 95.0 | — | — |
| Ru(5%)/C (0.25 g) | 54.0 | 78.0 | 9.0 | 2.0 |
| Pt(10%)/C (0.20 g) | 7.0 | 42.0 | 13.0 | — |
| Pd(5%)/C (0.21 g) | 4.0 | 65.0 | 8.0 | — |
| Rh(5%)/C (0.51 g) | 4.0 | 25.0 | — | — |
| Re(10%)/C (0.42 g) | 1.0 | 90.0 | — | — |

| Conditions: | |
|---|---|
| Solvent | 1,2-Dichloroethane, 15 mls. |
| O$_2$-Activator | 2-Ethyl-9,10-dihydro-9,10-dihydroxyanthracene, 4.2 g (17.7 mmols) |
| Cocatalyst | DDAB is Didecyldimethylammonium bromide, 0.94 g (2 mmols) |
| Oxidation Temp. | 70° C. |
| Air Pressure | 600 psi |
| Hydrogenation Temp. | 40° C. |
| Hydrogen Pressure | 450 psi |
| Substrate | 1-Dodecanol, 1.55 g (8.0 mmols) |
| Oxidation Reaction Time | 18 hrs. |

ILLUSTRATIVE EMBODIMENT IV

Utilizing the above-described experimental procedure, different solvents were used. The experimental conditions and the results are shown in Table 4 below (autoclave experiments).

TABLE 4

| Oxidation of 1- Dodecanol: Effect of Solvent | | | | | |
|---|---|---|---|---|---|
| | Cocat- | Conv. | Selectivity, % | | |
| Solvent | alyst | % | C$_{12}$-Aldehyde | C$_{12}$-Acid | C$_{24}$-Ester |
| 1,2-DCE$^1$ | DDAB | 74.0$^a$ | 95.0 | — | — |
| | DDAB | 4.0$^b$ | 65.0 | 8.0 | — |
| Toluene | DDAB | 60.0$^a$ | 12.0 | 27.0 | — |
| | — | 30.0$^b$ | 92.0 | 4.0 | — |
| N,N-DMF$^2$ | — | 8.0$^a$ | 78.0 | — | — |
| | — | 3.0$^b$ | 90.0 | — | — |

| Conditions | |
|---|---|
| Cocatalyst | DDAB is Didecyldimethylammonium bromide, 0.94 g (2 mmols) |
| Catalyst | (a)Ru(10%)/Al$_2$O$_3$, 0.19 g; (b)Pd(5%)/C, 0.21 g |
| O$_2$-Activator | 2-Ethyl-9,10-dihydro-9,10-dihydroxyanthracene, 4.17 g (17.1 mmols) |
| Substrate | 1-Dodecanol, 1.55 g (8.0 mmols) |
| Solvents (15 mls) | 1. 1,2-dichloroethane, 2. N,N-Dimethylformamide |

TABLE 4-continued

| | |
|---|---|
| Oxidation Temp. | 70° C. |
| Air Pressure | 600 psi |
| Hydrogenation Temp. | 40° C. |
| Hydrogenation Pressure | 450 psi |
| Oxidation Reaction Time | 18 hrs. |

What is claimed is:

1. A process for oxidation of primary saturated alcohols to a product consisting of aldehydes, acids, esters and mixtures thereof which comprises contacting a primary alcohol and molecular oxygen with a catalyst selected from the group consisting of ruthenium, rhodium, platinum, palladium, rhenium and mixtures thereof, optionally a cocatalyst comprising a quaternary alkyl ammonium bromide wherein the alkyl moieties have carbon numbers ranging from 1 to about 20 and an oxygen activator selected from the group consisting of dihydrodihydroxynaphthalene, dihydrodihydroxyanthracene and mixtures thereof, and subsequently separating from the reaction mixture the product aldehydes, acids and esters.

2. The process of claim 1 wherein the catalyst is supported on an inert porous support.

3. The process of claim 2 wherein the catalyst is supported on alumina or carbon.

4. The process of claim 1 wherein oxidized oxygen activator naphthoquinone or anthraquinone is separated from the reaction mixture, contacted with hydrogen and a hydrogenation catalyst whereby the naphthoquinone or anthraquinone is hydrogenated to the oxygen activator dihydrodihydroxynaphthalene or dihydrodihydroxyanthracene which is then recycled back to the oxidation reaction.

5. The process of claims 1 or 4 wherein the oxygen activator is selected form the group consisting of 2-ethyl-9,10-dihydro-9,10-dihydroxyanthracene, 2,3-dichloro-1,4-dihydro-1,4-dihydroxynaphthalene, disodium 6,7-dichloro-9,10-dihydro-9,10-dihydroxyanthracene-2,6-disulfonic acid and mixtures thereof.

6. The process of claims 1 or 4 wherein the hydrogenation is carried out at a temperature ranging form about 0° C. to about 100° C.

7. The process of claim 6 wherein the oxidation is carried out at a temperature ranging from about 50° C. to about 100° C.

* * * * *